United States Patent [19]
Pitzele et al.

[11] Patent Number: 4,933,369
[45] Date of Patent: Jun. 12, 1990

[54] DIMETHYL TYROSYL AMIDE SULFIDES, SULFOXIDES AND SULFONES

[75] Inventors: Barnett S. Pitzele; Nizal S. Chandrakumar; Donald W. Hansen, Jr., all of Skokie; Gilbert W. Adelstein, Evanston, all of Ill.

[73] Assignee: G. D. Searle & Co., Chicago, Ill.

[21] Appl. No.: 251,722

[22] Filed: Sep. 30, 1988

[51] Int. Cl.$^5$ .................. A61K 31/135; A61K 31/38; C07C 233/22; C07D 333/22
[52] U.S. Cl. .................................. 514/620; 514/438; 514/445; 514/446; 514/512; 514/542; 549/65; 549/77; 558/269; 560/42; 564/164; 564/165
[58] Field of Search .................. 564/165, 164; 549/77, 549/65; 514/438, 446, 620, 445, 512, 542; 558/269; 560/42

[56] References Cited
U.S. PATENT DOCUMENTS
4,599,325 7/1986 Hansen, Jr. et al. .................. 514/19

Primary Examiner—Richard L. Raymond
Assistant Examiner—P. O'Sullivan
Attorney, Agent, or Firm—Frank P. Grassler; Paul D. Matukaitis

[57] ABSTRACT

The present invention relates to new compounds of the formula

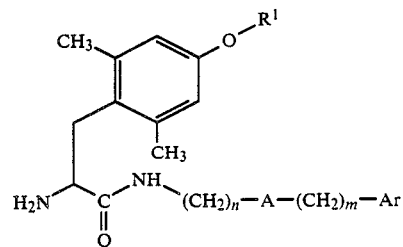

and the pharmaceutically acceptable salts thereof and the enantiomers thereof, wherein $R^1$ is H, lower alkyl, alkenyl, aralkyl, or $C(O)R^2$ wherein $R^2$ is lower alkyl, alkenyl, alkoxy, or aralkyl; n is an integer of from 2–4; m is an integer of from 0–4; A is $S(O)_x$ wherein x is an integer of from 0–2; and Ar is phenyl or thienyl. These compounds are useful as analgesics.

41 Claims, No Drawings

DIMETHYL TYROSYL AMIDE SULFIDES, SULFOXIDES AND SULFONES

BACKGROUND OF THE INVENTION

The present invention provides novel compounds, compositions, methods of their use and methods of their manufacture, such compounds believed to be pharmacologically useful to induce analgesia in mammals. More specifically, the compounds of the present invention are orally active dimethyl tyrosyl amide sulfides, sulfones and sulfoxides which, by acting as neurotransmitters or neuromodulators in the central nervous system central pain-suppressant system, induce analgesia.

Opioids are a group of drugs that are, to varying degrees, opium-like or morphine-like in their properties. The opioids are employed primarily as analgesics, but they have many other pharmacological effects as well, and they share some of the properties of certain naturally occurring peptides. By 1967, researchers had concluded that the complex interactions among morphine-like drugs, morphine antagonists, and mixed morphine agonist-antagonists could best be explained by postulating the existence of more than one type of receptor for the opioids and related drugs. Subsequent research revealed that there are three distinct families of opioid peptides, the endorphins, the enkephlins and the dynorphans, and multiple categories of opioid receptors. Although studies of the binding of opioid drugs and peptides to specific sites in brain and other organs has suggested the existence of perhaps as many as eight different types of opioid receptors, in the CNS there is reasonably firm evidence for three major categories of receptors, designated $\mu$, $\kappa$, and $\delta$.

The classical antagonist, naloxone, has been found to bind with high affinity to all opioid receptors although its affinity for $\mu$ receptors is generally more than ten times higher than for $\delta$ receptor sites. In 1975, Hughes and Kosterlitz described the isolation of two pentapeptides that exhibited morphine-like actions—actions that were specifically antagonized by naloxone. The same year, Goldstein and colleagues reported the presence of peptide-like substances in the pituitary gland with opioid activity. The peptide appears to act as a neurotransmitter or neuromodutator in the CNS. The natural peptide binds stereos specifically to partially purified brain opiate receptor sites, see for example, Bradberry et al., Nature, 260,793 (1976). The natural peptide is also highly active in bioassays for opiate activity but exhibits only weak, fleeting analgesic activity when injected directly into the brain of the rat, see for example, Belluzi et al., Nature, 260,625 (1976). In order to overcome the lack of in vivo activity, a number of investigators have made numerous modifications to methionine enkephalin, which was the original pentapeptide reported by Hughes et al. Among such modifications have been the synthesis and activity of short chain enkephalin-like peptides, among them tripeptide and dipeptide alkylamides by Kiso et al., "Peptide Chemistry 1981," 65-70, Protein Research Foundation, Osaka, Japan (1982). Vavrek, et al., Peptides 2,303, 1981, disclosed analogs of enkephalin, among them the dipeptide tyrosine-D-alanine-phenylpropylamide.

The compounds of this invention are non-peptide opioid agonists that act primarily at the $\mu$ receptor, having preferential affinity for the $\mu$ receptor over the $\delta$ receptor of 30-100 fold. The compounds of this invention have unexpected and surprisingly superior properties when compared to the di, tri, tetra and pentapeptides of the prior art. The present invention provides new tyrosyl amide sulfide, sulfoxide and sulfone derivatives which show improved potency as analgesic agents by both oral and parenteral routes of administration.

SUMMARY OF THE INVENTION

The invention relates to novel compounds of the general formula I:

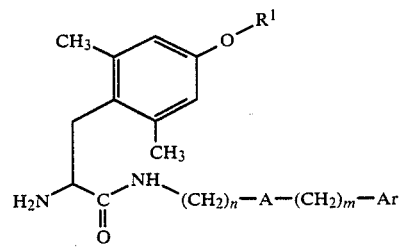

and the pharmaceutically acceptable salts thereof and the enantiomers thereof, wherein $R^1$ is H, lower alkyl, alkenyl or aralkyl, $C(O)R^2$ wherein $R^2$ is lower alkyl, alkenyl, alkoxy or aralkyl;

n is an integer of from 2-4; m is an integer of from 0-4; A is $S(O)_x$ wherein x is an integer of from 0-2; and Ar is phenyl or thienyl.

The compounds and pharmaceutical compositions thereof are useful in the analgesic methods of the invention.

DETAILED DESCRIPTION OF THE INVENTION

As used herein, the expressions "alkoxy", "alkenyloxy" or "arylalkyloxy" are defined to include straight or branched carbon-carbon linkages of 1-5 carbon atoms.

The term "pharmaceutically acceptable salts" refers to non-toxic salts of the compounds of this invention which are generally prepared by reacting the free base with a suitable organic or inorganic acid Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts.

As used herein, the term "analgesia" shall mean the absence of sensibility to pain, designating particularly the relief of pain without loss of consciousness.

Most especially preferred compounds of the present invention are those which are namely:

($\pm$)$\alpha$-amino-4-hydroxy-2,6-dimethyl-N-[2-[(3-phenylpropyl) thio]ethyl]benzenepropanamide, and which is of the structure

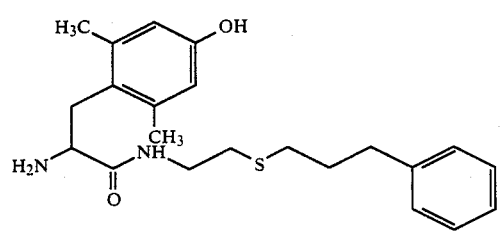

(L)α-amino-4-hydroxy-2,6-dimethyl-N-[3-(phenyl-thio)propyl]benzenepropanamide, and which is of the structure

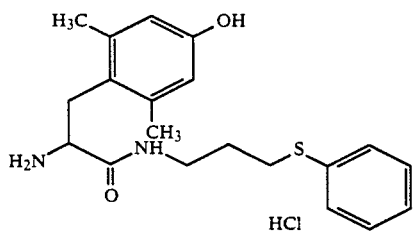

(±)α-amino-4-hydroxy-2,6-dimethyl-N-[3-(phenylmethyl) thio]propyl]benzenepropanamide, and which is of the structure

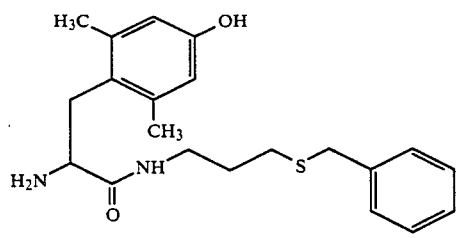

(±)α-amino-4-hydroxy-2,6-dimethyl-N-[3-[(2-phenylethyl) thio]propyl]benzenepropanamide, and which is of the structure

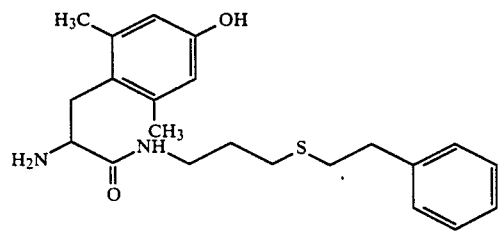

(±)α-amino-4-hydroxy-2,6-dimethyl-N-[4-[(phenylmethyl) thio]butyl]benzenepropanamide, and which is of the structure

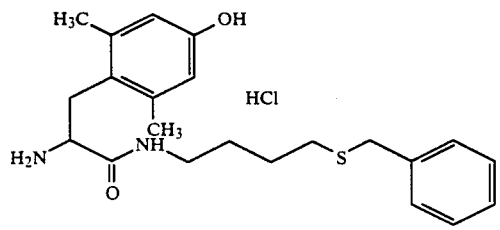

(±)α-amino-4-hydroxy-2,6-dimethyl-N-[2-[(3-phenylpropyl) sulfinyl]ethyl]benzenepropanamide, and which is of the structure

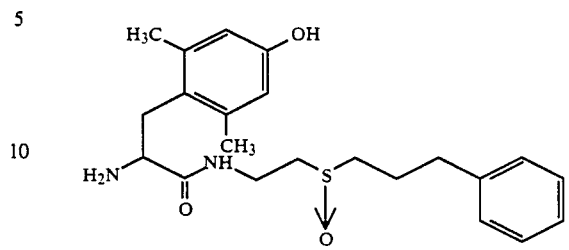

(±)α-amino-4-hydroxy-2,6-dimethyl-N-[3-[(2-phenylethyl) benzenepropanamide, and which is of the structure

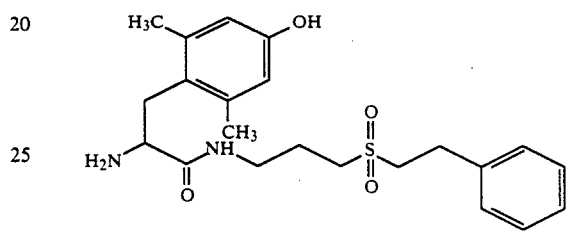

(±)α-amino-4-hydroxy-2,6-dimethyl-N-[2-[(3-phenylpropyl) sulfonyl]ethyl]benzenepropanamide, and which is of the structure

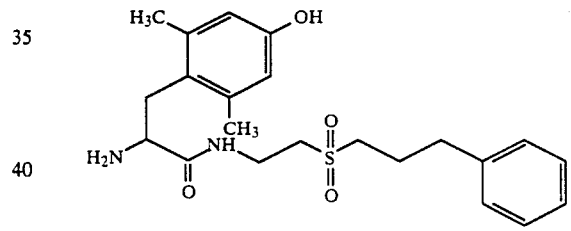

Compounds of the invention can be prepared readily according to one of the following reaction schemes or modifications thereof using readily available starting materials, reagents and conventional synthesis procedures. In these reactions, it is also possible to make use of variants which are in themselves known, but are not mentioned here in greater detail.

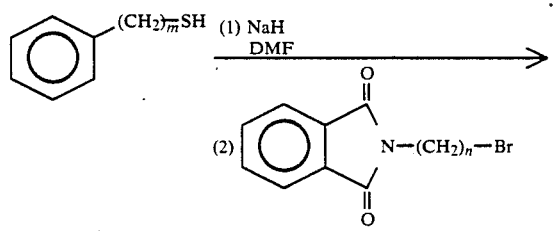

-continued
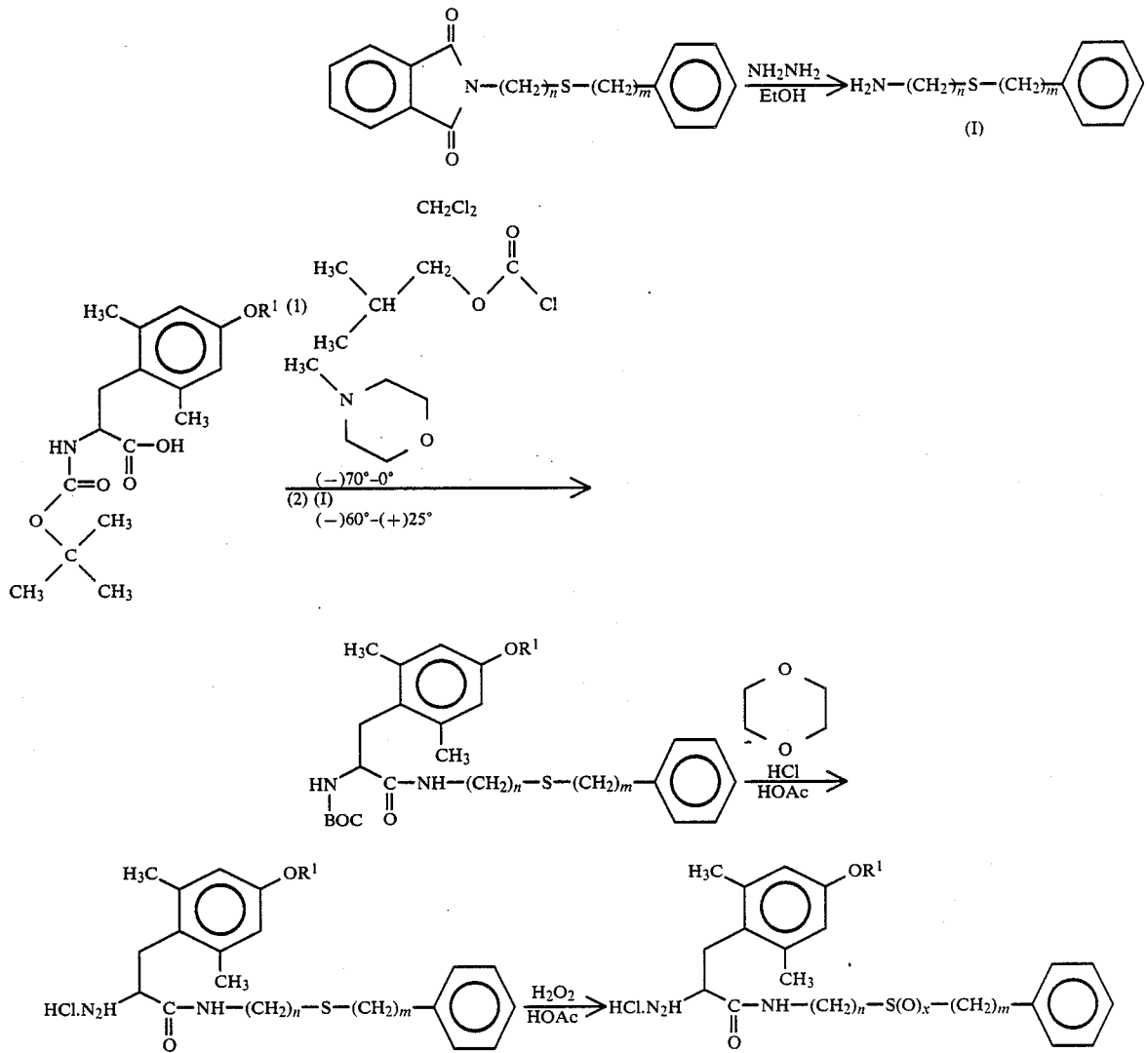
wherein
m = 0,1,2,3,4
n = 0,1,2,3,4
R¹ = H
x = 0,1,2
SCHEME II
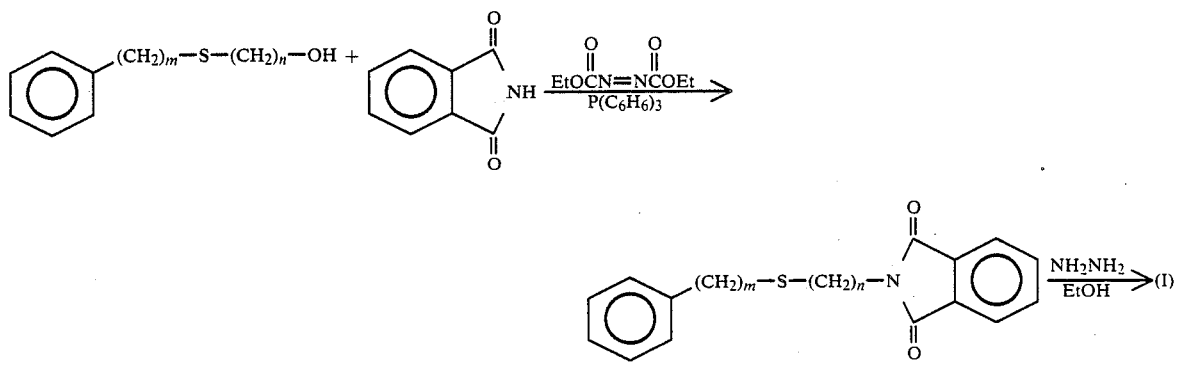

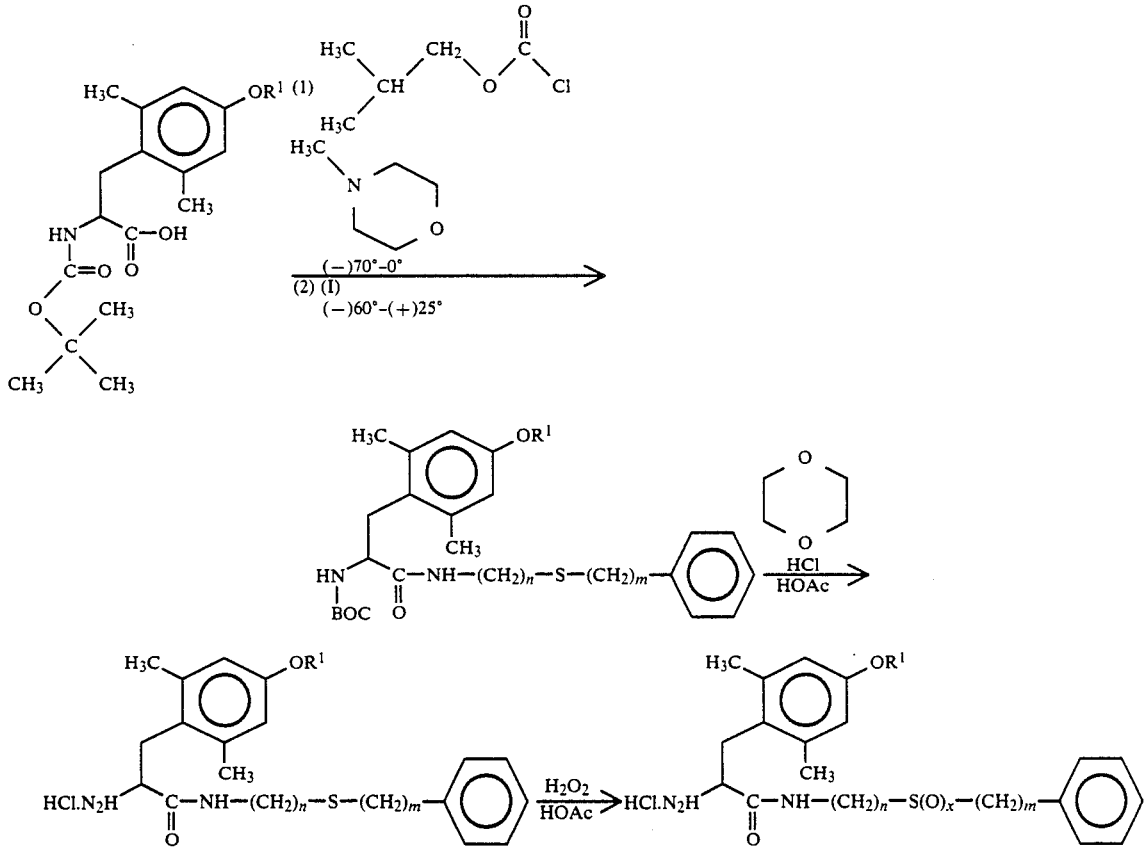

wherein
m = 0,1,2,3,4
n = 0,1,2,3,4
R¹ = H

The compounds of the present invention can be administered in such oral dosage forms as tablets, capsules, pills, powders, granules, elixirs, tinctures, syrups, emulsions and suspensions. Likewise, they may also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed in the induction of analgesia. The dosage regimen utilizing the compounds of the present invention is selected in accordance with a variety of factors including the type, species, age, weight, sex and medical condition of the patient. Other relevant factors are the severity of the condition to be treated, the route of administration, the renal and hepatic function of the patient, the route of administration and the particular compound employed or salt thereof. An ordinarily skilled veterinarian or physician can readily determine and prescribe an effective amount of the drug required to induce analgesia.

Dosages of the compounds of the present invention, when used for the indicated analgesia effects, will range between about 1 mg/kg/day to about 1,000 mg/kg/day and preferably 10-100 mg/kg/day. Advantageously, the compounds of the present invention may be administered in a single daily dose or the total daily dosage may be administered in divided doses of 2, 3 or 4 times daily.

In the pharmaceutical compositions and methods of the present invention, the foregoing compounds described in detail above will form the active ingredients and will typically be administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of tablets or capsules, the active drug component may be combined with an oral non-toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form the active drug components may be combined with any oral non-toxic pharmaceutically acceptable inert carrier such as ethanol, glycerol, water and the like. Moreover, when desired or necessary, suitable binders, lubricants, disintegrating agents and coloring agents can also be incorporated in the mixture. Suitable binders include starch, gelatin, natural sugars such as glucose or beta lactose, corn sweeteners, natural and synthetic gums such as acacia, tragacanth or sodium alginate, carboxymethylcellulose, polyethylene glycol and various waxes. Lubricants for use in these dosage forms include boric acid, sodium benzoate, sodium acetate, sodium chloride and the like. Disintegrators include, without limitation, starch, methylcellulose, agar, bentonite, xanthan gum and the like.

Pharmacologic Activity

The compounds of this invention exhibit analgesic properties useful in the treatment of pain. The test procedures employed to measure this activity of the compounds of the present invention are described below.

Writhing Assay

Male Charles River albino mice (CD-1/HAM/lLR) weighing between 20 and 30 grams were used. Thirty minutes after subcutaneous or intragastric administration of the test compound (0.1 ml/10 gm body weight), 0.025% (w/x) phenylbenzoquinone was injected intraperitoneally (0.1 ml/10 gm body weight). Five minutes later, each mouse was placed in a large glass beaker and the number of writhes that occurred in the subsequent ten minutes is counted. A writhe consisted of dorsoflexion of the back, extension of the hind limbs and strong contraction of the abdominal musculature. The test compound was considered to have produced analgesia in a mouse if the number of writhes elicited by phenylbenzoquinone was equal to or less than ½ the median number of writhes recorded for the saline-treated group that day. The results were expressed as the number of mice (out of a possible 10) in which the test compound produced analgesia. The test compound was rated active if the number of writhes in the drug treatment group was significantly less than the number of writhes in the saline treatment group as determined by a one-way analysis of variance. If the initial test dose of 2 mg/kg inhibited writhing in greater than six out of ten mice, the effect of additional doses was evaluated and an $ED_{50}$ value was calculated using a maximum likelihood function.

Opiate Binding Assay

The test compounds were evaluated for their ability to displace the binding of $^3$H-Naloxone to opiate receptors isolated from rat brain. Male rats (Crl:CD)(SD)(BR) obtained from Charles River Laboratories (Portage, Mich.) were sacrificed by cervical dislocation. A purified homogenate of receptor membranes was prepared from the brains according to the method described by Chang and Cuatrecasas. Multiple Opiate Receptors: Enkephalins and Morphine Bind to Receptors of Different Specificity. *J. Biol. Chem.* 254, 2610–2618 (1979). The brains were homogenized in ten volumes of 0.32 M sucrose and centrifuged twice at 6,000×g for fifteen minutes. Following centrifugation of the supernatants at 40,000×g for thirty minutes, the pellets were resuspended in 5 mM tris HCl, and centrifuged at 6,000×g. The supernatant was centrifuged at 40,000×g. The resuspension in 5 mM tris and centrifugation was repeated twice. The final pellet was resuspended in two volumes of 50 mM tris HCl, (pH 7.4). The homogenate was assayed for protein content according to the method of Itzhaki and Gill (R. E. Itzhaki and D. N. Gill. A Micro-Biuret Method for Estimating proteins *Anal. Biochem.* 9, 401–410, 1964).

The binding of the test compounds to the receptor membrane preparation was measured using a modification of the method of Pert and Snyder (C. B. Pert and S. H. Snyder. Property of Opiate-Receptor Binding in Rat Brain. *Proc. Natl. Acad. Sci.* 70, 2243–2247, 1973). The receptor assay was run using a final concentration of 1NM $^3$H-Naloxone and 0.5 mg/ml of homogenate protein. Levorphanol ($1 \times 10^{-5}$M) was used as the displacer for non-specific binding. The final concentration of the test compounds was $10^{-5}$M) The assay was run in 0.05 M tris HCl (pH 7.4). Total assayed volume was 1.0 ml.

Samples were incubated at 25° C. for sixty minutes, filtered over Whatman GF/C glass fiber filters and rinsed twice with 2.4 ml washes of ice-cold buffer. The filters were air dried at 50° C. for thirty minutes. After drying, 10 ml of PCS was added to the vial and radioactivity determined using a Tracore Analytic Mark III liquid scintillation counter with a counting efficiency of 48%.

The $IC_{50}$ values, the concentration of the test compounds which inhibited $^3$H-Naloxone specific binding to the opiate receptor by 50%, were obtained from log-logit plots of concentration-response curves.

TABLE I

| | WRITHING ASSAY | | |
|---|---|---|---|
| EXAMPLE # | SUBCUTANEOUS DOSING | INTRAGASTRIC DOSING | ACTIVE |
| 2 | + | | − |
| 2 | | + | − |
| 4 | + | | + |
| 4 | | + | − |
| 3 | + | | + |
| 3 | | + | − |
| 5 | + | | + |
| 5 | | + | − |
| 6 | + | | − |
| 6 | | + | − |
| 7 | + | | + |
| 7 | | + | − |
| 8 | + | | + |
| 8 | | + | − |

TABLE II

| OPIATE BINDING ASSAY | | |
|---|---|---|
| EXAMPLE # | $IC_{50}$ | ACTIVE |
| 2 | $2.2 \times 10^{-9}$ | + |
| 4 | $2.8 \times 10^{-9}$ | + |
| 3 | $8 \times 10^{-10}$ | + |
| 6 | $9 \times 10^{-10}$ | + |
| 7 | $2.1 \times 10^{-8}$ | + |
| 5 | $3.6 \times 10^{-9}$* | + |
| 9 | $20.9 \times 10^{-9}$* | + |

*The radioactive ligand in this particular assay was (D)Ala$^2$-Glyol$^5$Enkephlin.

the following non-limiting examples further details for the preparation of the compounds of the present invention. Those skilled in the art will readily understand that known variations of the conditions and processes of the following preparative procedures can be used to prepare these compounds. All temperatures are degrees Celsius unless otherwise noted. Unless otherwise noted, IR and NMR spectra were consistent with the assigned structure.

EXAMPLE A

2-[2-[(3-phenylpropyl)thio]ethyl]-1H-isoindole-1,3(2H)-dione

Sodium hydride (60% by weight in an oil dispersion, 11.67 g, 292 mmol) was weighed into a 1 L round-bottom single-neck flask. Mixed hexanes (900 ml) were added, and the suspension stirred with a magnetic stirrer. After 20 minutes, stirring was stopped and the NaH was allowed to settle. The supernatant was then decanted to remove the mineral oil. Dry DMF (300 ml) was added. 3-phenyl-n-propylmercaptan (40.4 g, 40 ml, 265 mmol) was then added carefully. After addition was complete, the mixture was stirred 10 minutes. A solution of 2-bromoethylphthalimide (70.8 g, 279 mmol) in DMF (320 ml) was then added rapidly, and the resulting mixture was protected with a drying tube and stirred at room temperature overnight. The reaction mixture was diluted to 1.7 L with 1% NaOH in H$_2$O. This mixture was extracted thrice with diethyl ether. The extracts were combined, extracted with 1%, aq. NaOH, then with saturated brine. The ethereal solution was dried (MgSO$_4$), filtered, and concentrated at low pressure to a syrup. This syrup was chromatographed on silica with ethyl acetate-hexane eluents. The title compound was eluted with 15:85 ethyl acetate-hexane. The resulting oil was used directly in Example B.

EXAMPLE B

2-[(3-phenylpropyl)thio]ethanamine

The product of Example A (33.0 g, 100.6 mmol) was refluxed in ethanol (1 L) in the presence of hydrazine hydrate (20.2 g, 402.4 mmol) for 4.5 hours. The reaction mixture was cooled and filtered. The solid was washed with ethanol. The filtrate and solid were combined and stripped at reduced pressure. The resulting mass was repeatedly triturated with diethyl ether. The ether fractions were combined, filtered, and stripped at reduced pressure to give the title compound as a yellow oil.

EXAMPLE C

2-[3-[(2-phenylethyl)thio]propyl]-1H-isoindole-1,3(2H)-dione 2-phenylethylmercaptan was reacted with sodium hydride, and then with 3-bromoprop.lyphthalimide as described in Example A. No column chromatography has required. NMR (80 MHz, CDCl$_3$, δ in ppm from TMS): methylene bonded to nitrogen δ 3.75; methylenes bonded to sulfur, δ 2.80, benzyl methylene δ 2.55; methylene bonded to carbons δ 1.94. IR (CDCl$_3$) 1712 vvs, 1772 m cm$^{-1}$.

EXAMPLE D

3-[(2-phenylethyl)thio]propanamine

The title compound of Example C was subjected to the conditions described in Example B. This yielded the title compound as a yellow oil.

EXAMPLE E

2-[3-(phenylthio)propyl]-1H-isoindole-1,3(2H)-dione

Diethyl azodicarboxylate (14 ml, 89 mmol) was added over 3 minutes to a stirred solution of 3-phenylthiopropanol (14.91 g, 89 mmol), triphenylphosphine (23.25 g, 89 mmol) and phthalimide (13.05 g, 89 mmol) in tetrahydrofuran (350 ml) at room temperature. After 15 hours, the mixture was concentrated in vacuo. Flash chromatography of the residue, eluting with 1:1 ether/hexane, gave the title compound as a white solid (22.5 g 85%). NMR (200 MHz, CDCl$_3$): δ 2.0 (q, 2H), 2.95 (t, 2H), 3.85 (t, 2H), 7.25 (m, 5H), 7.8 (m, 4H).

EXAMPLE F

3(phenylthio)propanamine

The title compound of Example E was subjected to the conditions described in Example B. This yielded the title compound. NMR (300 MHz, CDCl$_3$): δ 1.15 (bs, 2H), 1.8 (q, 2H), 2.8 (t, 2H), 3.0 (t, 2H), 7.3 (m, 5H).

EXAMPLE G

2-[3-[(phenylmethyl)thio]propyl]-1H-isoindole-1,3(2H)-dione

The preparation described in Example C was repeated, with benzyl mercaptan replacing 2-phenyl mercaptan. This yielded the title compound, NMR (CDCl$_3$): phthalyl aromatic protons, multiple at δ 7.8, phenyl protons δ 7.25 methylenes bonded to sulfur δ 3.7.

EXAMPLE H

3-[(phenylmethyl)thio]propanamine

The title compound of Example G was subjected to the conditions described in Example B, yielding the title compound. NMR (CDCl$_3$) thiobenzyl methylene δ 3.7; methylene on nitrogen, δ 2.7; methylene on sulfur, δ 2.45.

EXAMPLE I

2-[4-[(phenylmethyl)thio]butyl]-1H-isoindole-1,3(2H)-dione

Benzyl mercaptan (8.2 g, 66.4 mmol) was reacted with sodium hydride (52.4% in oil, 3.35 g, 73.0 mmol), and then with N-(4-bromobutyl)-phthalimide (19.7 g, 69.7 mmol) as described in Example A, to give the title compound. NMR (CDCl$_3$): thiobenzyl methylene, and methylene bonded to nitrogen, both at δ 3.7. Methylene bonded to sulfur at δ 2.4.

EXAMPLE J

4-[(phenylmethyl)thio]butanamine

The title compound of Example I was subjected to the conditions of Example B, giving the title compound. NMR (CDCl$_3$): thiobenzyl methylene δ 3.7, methylene connected to nitrogen, δ 2.7; methylene connected to sulfur δ 2.4.

EXAMPLE 1

(±)-[[(1,1-dimethylethoxy)carbonyl]amino]-4-hydroxy-2,6-dimethyl-N-[2-[(3-phenylpropyl)thio]ethyl]benzenepropanamide A 500 ml round-bottom, three-necked flask was fitted with a magnetic stirrer, a thermometer, a pressure equilibration dropping funnel, and a y-tube to which was attached a drying tube and a N$_2$ inlet. The flask was charged with methylene chloride (150 ml), molecular sieves (5A, 8–12 mesh beads, 15.8 g), and N-BOC-2,6-dimethyl-(DL)-tyrosine (10 g, 32.3 mmol). The mixture was stirred under N$_2$, and N-methyl-morpholine (3.47 g, 34.3 mmol) was added dropwise at room temperature.

After stirring 10 minutes, the reaction mixture was cooled to −60° C. Isobutyl chloroformate (4.42 g, 33.3 mmol) was added dropwise. The reaction mixture was stirred at low temperature for 10 minutes, then the temperature was brought up to 0° and maintained there for 45 minutes. The reaction temperature was then returned to −60°, and the title compound of Example B (6.72 g, 34.3 mmol) was added as a solution in methylene chloride (75 ml). After stirring at low temperature for one hour, the cold bath was removed and the mixture stirred at room temperature 18 hours. The mixture was then filtered, and the solid was washed with CH$_2$Cl$_2$ (150 ml). The filtrate and wash were combined and extracted thrice with 150 ml portions of 0.5M KHSO$_4$. The aqueous phases were combined and back-washed with CH$_2$Cl$_2$ (200 ml). The organic phases were combined, dried (MgSO$_4$), filtered, and stripped to a gum.

This gum was subjected to column chromatography on silica gel. The title compound was eluted with 40:60 ethyl acetate-hexane. NMR (DMSO-d$^6$, 80 MHz, δ in ppm from TMS) δ 1.30 (BOC methyls); δ 2.18 aromatic methyls, δ 2.55 methylene on sulfur.

For C$_{27}$H$_{38}$N$_{2l}$O$_4$S (mw 488): Calc. C 66.64; H 7.87; N 5.76; S 6.59. Found C 66.28; H 7.88; N 5.66; S 6.42.

EXAMPLE 2

(±)α-amino-4-hydroxy-2,6-dimethyl-N-[2-[(3-phenylpropyl) thio]ethyl]benzenepropanamide The title compound of Example 1 (9 g, 18.4 mmol) was dissolved in methanol (70 ml). A solution of HCl in dioxane (6.8 N, 15 ml) was added. The mixture was stirred at room temperature 19 hours. The solution was then stripped at low pressure. The resulting residue was dissolved in aqueous methanol, filtered, and stripped again. This residue was dissolved in a minimum amount of methanol. The volume was carefully trebled with water. The solution was lyophilized. The resulting material was dried in a vacuum desiccator at low pressure for 20 hours, giving the title compound as the hydrated HCl salt: NMR (DMSO-d$^6$, 80 MHz) δ 2.18 aromatic methyls; δ 6.40 aromatic protons on tyrosine; δ 3.00 methylene on nitrogen, δ 2.25–2.75 methylene of sulfur and benzyl-methylene on unsubstituted phenyl group.

For C$_{22}$H$_{30}$N$_2$O$_2$S.HCl.¼H$_2$O (mW 427.52): Calc. C 61.81; H 7.43; N 6.55; CL 8.29; S 7.50. Anal. C 61.77; H 7.69; N 6.45; CL 8.52; S 7.46.

EXAMPLE 3

(±)α-amino-4-hydroxy-2,6-dimethyl-N-[2-[(3-phenylpropyl)sulfonyl]ethyl]benzenepropanamide The title compound of Example 2 (1.0 g, 2.34 mmol) was dissolved in methanol (10 ml). Hydrogen peroxide (30% in H$_2$O, 2.13 ml, 18.7 mmol) was added and the solution was stirred for 3 hours. The mixture was then concentrated at low pressure, diluted with H$_2$O, shelled, and lyophilized, giving the title compound as its HCl salt.

For C$_{22}$H$_{30}$N$_2$O$_4$S-HCl (mw 455.02): Calc. C 58.07; H 6.87; N 6.16; CL 7.79; S 7.05. Found C 57.83; H 7.12; N 6.02; CL 7.94; S 7.02.

EXAMPLE 4

(±)α-amino-4-hydroxy-2,6-dimethyl-N-[2-[(3-phenylpropyl)sulfinyl]ethyl]benzenepropanamide The title compound of Example 2 (2.0 g, 4.68 mmol) was dissolved in methanol (20 ml). Hydrogen peroxide (30%, 0.53 g, 4.68 mmol) was added. The mixture was stirred at room temperature overnight. The solution was then stripped at reduced pressure, and subjected to column chromatography on silica gel. The title compound was eluted with ethanol: CH$_2$CL$_2$: conc. aq. NH$_4$OH 5:85:0.5.

For C$_{22}$H$_{30}$N$_2$O$_3$S.½H$_2$O: Calc. C 64.20; H 7.59; N 6.81; S 7.79. C 63.80; H 7.44; N 6.78; S 7.93.

EXAMPLE 5

(±) α-2,6-dimethyl-N-[3-[(2-phenylethyl)thio]propyl]benzenepropanamide

The N-BOC-precursor of the title compound was prepared according to the method of Example 1, using the title compound of Example D in place of the title compound of Example B. The resulting BOC-precursor was exposed to the conditions described in Example 2, to produce the title compound as its hydrochloride salt. NMR (DMSO-d$^6$): methylene bonded to nitrogen δ 2.95; methylenes bonded to sulfur, δ 2.18; aromatic methyls δ 2.18; aromatic protons on tyrosine δ 6.43.

For C$_{22}$H$_{30}$N$_2$O$_2$S.HCl.½H$_2$O: Calc. C 61.16; H 7.47; N 6.48; CL 8.21; S 7.42. Found C 61.22; H 7.43; N 6.50; CL 8.48; S 7.45.

EXAMPLE 6

(±)α-amino-4-hydroxy-2,6-dimethyl-N-[3-[(2-phenylethyl)sulfonyl]-propyl]benzenepropanamide The title compound of Example 5 was treated as described in Example 3, giving the title compound as its hydrated hydrochloride salt. NMR (DMSO-d$^6$) methylene bonded to nitrogen δ 2.93, methylenes bonded to sulfur, δ 3; aromatic methyls 6 2.18; aromatic protons on tyrosine δ 6.40.

For C$_{22}$H$_{30}$N$_2$O$_4$S.HCl.¾H$_2$O: Calc. C 56.40; H 6.99; N 5.98; S 6.84; CL 7.57. Found C 56.34; H 7.22; N 5.94; S 7.11; CL 7.57.

EXAMPLE 7

(±)α-amino-4-hydroxy-2,6-dimethyl-N-[3-[(phenylmethyl)thio]propyl]benzenepropanamide The N-BOC-precursor of the title compound was prepared from the title compound of Example H according to the method of Example 1. The resulting BOC-protected peptide was exposed to the conditions of Example 2, to produce the title compound as its hydrated hydrochloride salt. NMR (DMSO-d$^6$) methylene bonded to nitrogen, tyrosyl benzyl methylene, both at δ 2.9–3.1 thiobenzyl methylene at δ 3.7, aromatic methyl δ 2.2.

For C$_{21}$H$_{28}$N$_2$SO$_2$.HCl.¼H$_2$O: Calc. C 61.00; H 7.19; N 6.77; CL 8.57; S 7.75. Found C 60.95; H 7.13; N 6.76; CL 8.62; S 7.82.

EXAMPLE 8

(±)α-amino-4-hydroxy-2,6-dimethyl-N-[4-(phenylmethyl)thio]butyl]benzenepropanamide The N-BOC-precursor of the title compound was prepared from the title compound of Example according to the method of Example 1. The resulting BOC protected peptide was exposed to the conditions of Example 2, to produce the title compound as its hydrated hydrochloride salt. NMR (DMSO-d$^6$): thiobenzyl methylene δ 3.7. Methylene bonded to nitrogen δ 3.0. Aromatic methyls at δ 2.2. Terminal phenyl group δ 7.3.

For C$_{22}$H$_{30}$N$_2$SO$_2$.HCl.¼H$_2$O: Calc. C 61.81; H 7.43; N 6.55; CL 8.27; S 7.50. Found C 61 73; H 7.42; N 6.38; CL 8.67; S 7.52.

EXAMPLE 9

(L)α-amino-4-hydroxy-2,6-dimethyl-N-[3-(phenylthio)propyl]benzenepropanamide

The N-BOC-precursor of the title compound was prepared from the title compound of Example F according to the method of Example 1, with the exception that BOC-(L)-2,6-dimethyl tyrosine was used. The resulting BOC-protected peptide was exposed to the conditions of Example 2, to produce the title compound as its hydrated hydrochloride salt.

NMR (400 MHz, DMSO-d$^6$): δ 1.5 (m, 2H), 2.7 (m, 2H), 2.95 (m, 3H), 3.15 (m, 1H), 3.65 (dd, 1H), 6.4 (h, 2H), 8.0 (t, 1H), 8.5 (bs, 3H).

[α]$589$ = +97.7 (1.023% in methanol)
[α]$365$ = +364.9 (1.023% in methanol)

For $C_{20}H_{26}N_2O_2S \cdot HCl \cdot \frac{1}{2}H_2O$: Calc. C 59.47; H 6.98; N 6.93; CL 8.78; S 7.94. Found C 59.58; H 6.94; N 6.84; CL 8.99; S 7.81.

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated to induce analgesia, dosage related adverse effects, if any, and analogous considerations. Likewise, the specific pharmacological responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invention. It is intended therefore that the invention be limited only by the scope of the claims which follow, and that such claims be interpreted as broadly as is reasonable.

What is claimed is:

1. A compound according to the general formula

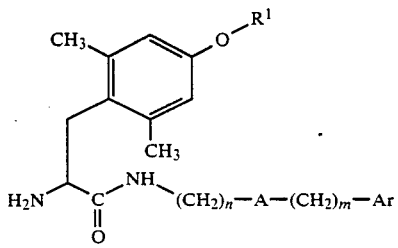

and the pharmaceutically acceptable salts thereof, and the enantiomers thereof, wherein
R$^1$ is H, lower alkyl, alkenyl or C(O)R$^2$ wherein R$^2$ is lower alkyl, alkenyl, or alkoxy
n is an integer of from 2 to 4; m is an integer of from 0 to 4; A is S(O)$_x$ wherein x is an integer of from 0 to 2; and Ar is phenyl.

2. The compound as claimed in claim 1, wherein R$^1$ is H.

3. The compound as claimed in claim 1, wherein n is 2.

4. The compound as claimed in claim 1, wherein n is 3.

5. The compound as claimed in claim 1, wherein n is 4.

6. The compound as claimed in claim 1, wherein A is S.

7. The compound as claimed in claim 1, wherein A is SO.

8. The compound as claimed in claim 1, wherein A is SO$_2$.

9. The compound as claimed in claim 1, wherein m is 0.

10. The compound as claimed in claim 1, wherein m is 1.

11. The compound as claimed in claim 1, wherein m is 2.

12. The compound as claimed in claim 1, wherein m is 3.

13. The compound as claimed in claim 1, wherein m is 4.

14. The compound as claimed in claim 1, wherein Ar is phenyl.

15. The compound as claimed in claim 1, and which is the hydrochloride salt thereof.

16. A compound as claimed in claim 1, namely (±)α-amino-4-hydroxy-2,6-dimethyl-N-[2-[(3-phenylpropyl)-thio]ethyl]benzenepropanamide and which is of the structure

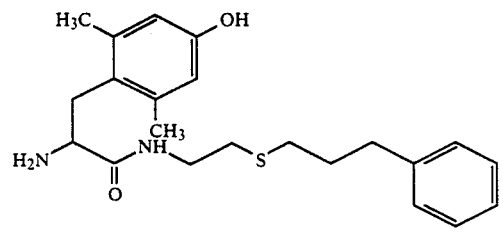

17. A compound as claimed in claim 1, namely (L)α-amino-4-hydroxy-2,6-dimethyl-N-[3-(phenylthio)-propyl]benzenepropanamide hydrochloride, and which is of the structure

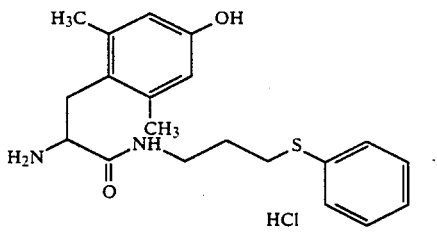

18. A compound as claimed in claim 1, namely (±)α-amino-4-hydroxy-2,6-dimethyl-N-[3-[(phenylmethyl)-thio]propyl]benzenepropanamide and which is of the structure

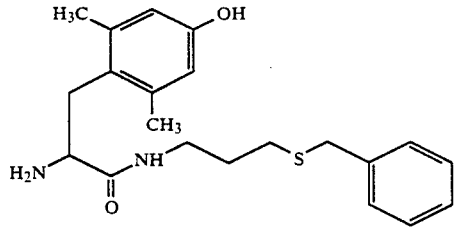

19. A compound as claimed in claim 1, namely (±)α-amino-4-hydroxy-2,6-dimethyl-N[3-[(2-phenylethyl)thio]propyl]benzenepropanamide and which is of the structure

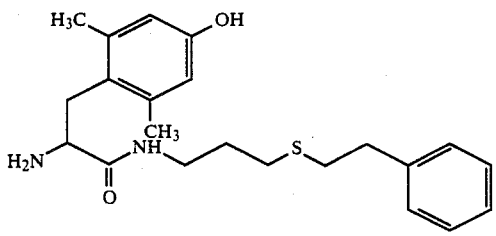

20. A compound as claimed in claim 1, namely (±)α-amino-4-hydroxy-2,6-dimethyl-N-[4-[(phenylmethyl)thio]butyl]benzenepropanamide hydrochloride and which is of the structure

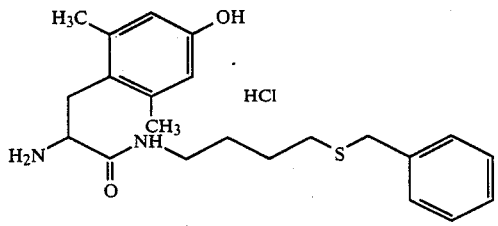

21. A compound as claimed in claim 1, namely (±)α-amino-4-hydroxy-2,6-dimethyl-N-[2-[(3-phenylpropyl)sulfinyl]ethyl]benzenepropanamide and which is of the structure

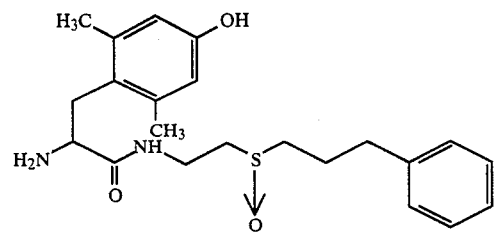

22. A compound as claimed in claim 1, namely (±)α-amino-4-hydroxy-2,6-dimethyl-N-[3-[(2-phenylethyl)sulfonyl]propyl]benzenepropanamide and which is of the structure

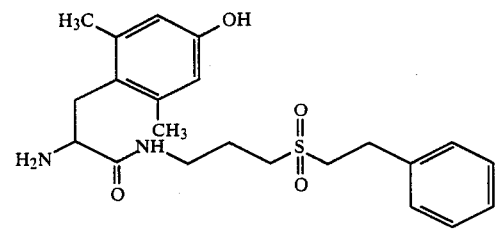

23. A compound as claimed in claim 1, namely (±)α-amino-4-hydroxy-2,6-dimethyl-N-[2-[(3-phenylpropyl)sulfonyl]ethyl]benzenepropanamide and which is of the structure

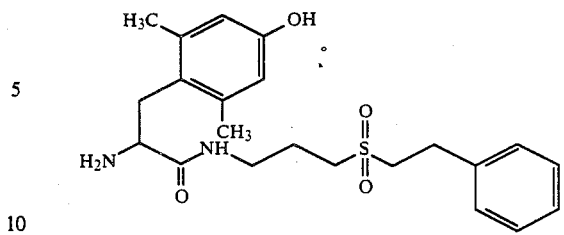

24. A pharmaceutical composition comprised of a pharmaceutically acceptable non-toxic carrier in combination with a compound according to claim 1.

25. The composition as claimed in claim 24, wherein said compound is (±)α-amino-4-hydroxy-2,6-dimethyl-N-[2-[(3-phenylpropyl)thio]ethyl]benzenepropanamide.

26. The composition as claimed in claim 24, wherein said compound is (L)α-amino-4-hydroxy-2,6-dimethyl-N-[3-(phenylthio)propyl]benzenepropanamide.

27. The composition as claimed in claim 24, wherein said compound is (±)α-amino-4-hydroxy-2,6-dimethyl-N-[3-(phenylmethyl)thio]propyl]benzenepropanamide.

28. The composition as claimed in claim 24, wherein said compound is (±)α-amino-4-hydroxy-2,6-dimethyl-N-[3-[(2-phenylethyl)thio]propyl]benzenepropanamide.

29. The composition as claimed in claim 24, wherein said compound is (±)α-amino-4-hydroxy-2,6-dimethyl-N-[4-[(phenylmethyl)thio]butyl]benzenepropanamide.

30. The composition as claimed in claim 24, wherein said compound is (±)α-amino-4-hydroxy-2,6-dimethyl-N-[2-[(3-phenylpropyl)sulfinyl]ethyl]benzenepropanamide.

31. The composition as claimed in claim 24, wherein said compound is (±)α-amino-4-hydroxy-2,6-dimethyl-N-[3-[(2-phenylethyl)sulfonyl]propyl]benzenepropanamide.

32. The composition as claimed in claim 24, wherein said compound is (±)α-amino-4-hydroxy-2,6-dimethyl-N-[2-[(3-phenylpropyl)sulfonyl]ethyl]benzenepropanamide.

33. A method of inducing analgesia in a mammal in need thereof, comprising administering to said mammal a pharmacologically effective amount of a compound as claimed in claim 1.

34. The method as claimed in claim 33, wherein said compound is (±)α-amino-4 hydroxy-2,6-dimethyl-N-[2-[(3-phenylpropyl)thio]ethyl]benzenepropanamide.

35. The method as claimed in claim 33, wherein said compound is (L)α-amino-4-hydroxy-2,6-dimethyl-N-[3-(phenylthio)propyl]benzenepropanamide.

36. The method as claimed in claim 33, wherein said compound is (±)α-amino-4-hydroxy-2,6-dimethyl-N-[3-(phenylmethyl)thio]propyl]benzenepropanamide.

37. The method as claimed in claim 33, wherein said compound is (±)α-amino-4-hydroxy-2,6-dimethyl-N-[3-[(2-phenylethyl)thio]propyl]benzenepropanamide.

38. The method as claimed in claim 33, wherein said compound is (±)α-amino-4-hydroxy-2,6-dimethyl-N-[4-[(phenylmethyl)thio]butyl]benzenepropanamide.

39. The method as claimed in claim 33, wherein said compound is (±)α-amino-4-hydroxy-2,6-dimethyl-N-[2-[(3-phenylpropyl)sulfinyl]ethyl]benzenepropanamide.

40. The method as claimed in claim 33, wherein said compound is (±)α-amino-4-hydroxy-2,6-dimethyl-N-[3-[(2-phenylethyl)sulfonyl]propyl]benzenepropanamide.

41. The method as claimed in claim 33, wherein said compound is (±)α-a mino-4-hydroxy-2,6-dimethyl-N-[2-[(3-phenylpropyl)sulfonyl]ethyl]benzenepropanamide.

* * * * *

UNITED STATES PATENT AND TRADEMARK OFFICE
CERTIFICATE OF CORRECTION

PATENT NO. : 4,933,369
DATED : June 12, 1990
INVENTOR(S) : Pitzele, et al.

It is certified that error appears in the above-identified patent and that said Letters Patent is hereby corrected as shown below:

Column 1, line 38, reading "6 receptor sites" should read -- δ receptor sites --.

Column 1, line 46, reading "stereos specifically" should read -- stereospecifically --.

Column 1, line 67, reading "6 receptor" should read -- δ receptor --.

Column 3, the last two structures representing part of a reaction scheme, are incorrectly placed in the patent. These structures should be deleted from this column and inserted at the bottom of column 4 instead.

Column 4, line 16, reading "phenylethyl)benzenepropanamide" should read -- phenylethyl)sulfonyl|propyl}benzenepropanamide --.

Column 5, the fourth structure, that portion of the structure reading

UNITED STATES PATENT AND TRADEMARK OFFICE
CERTIFICATE OF CORRECTION

PATENT NO. : 4,933,369

DATED : June 12, 1990

INVENTOR(S) : Pitzele, et al.

It is certified that error appears in the above-identified patent and that said Letters Patent is hereby corrected as shown below:

This error regarding the misplacement of the dot (•) occurs in various instances throughout the remainder of the patent.

Column 8, line 62, reading "beta lactose" should read -- beta-lactose --.

Column 10, line 48, reading "the following non-limiting examples further details" should read -- The following non-limiting examples further illustrate details --.

Column 11, line 34, reading "3-bromoprop.lyphthalimide" should read -- 3-bromopropylphthalimide --.

Column 13, line 8, reading "$C_{27}H_{38}N_{21}\ O4^S$" should read -- $C_{27}H_{38}N_2O_4S$ --.

Column 13, line 27, reading "of sulfur" should read -- on sulfur --.

Column 13, line 29, reading "(mW 427.52)" should read -- (mw 427.52) --.

UNITED STATES PATENT AND TRADEMARK OFFICE
CERTIFICATE OF CORRECTION

PATENT NO. : 4,933,369
DATED : June 12, 1990
INVENTOR(S) : Pitzele, et al.

It is certified that error appears in the above-identified patent and that said Letters Patent is hereby corrected as shown below:

Column 13, line 58, reading "5:85:0.5" should read -- 15:85:0.5 --.

Column 13, line 63, reading "α-2,6-dimethyl" should read -- α-amino-4-hydroxy-2,6-dimethyl- --.

Column 14, line 19, reading "methyls 6 2.18" should read -- methyls δ 2.18 --.

Column 14, lines 43-44, reading "[4-(phenylmethyl)" should read -- [4-[(phenylmethyl) --.

Column 14, lines 46-47, reading "Example according" should read -- Example J according --.

Column 16, line 66 (Claim 19), reading "-N[3-" should read -- -N-[3- --.

Column 18, Claim 23, that portion of the structure reading

UNITED STATES PATENT AND TRADEMARK OFFICE
CERTIFICATE OF CORRECTION

PATENT NO. : 4,933,369

DATED : June 12, 1990

INVENTOR(S) : Pitzele, et al.

It is certified that error appears in the above-identified patent and that said Letters Patent is hereby corrected as shown below:

Column 18, line 44 (Claim 34), reading "-4 hydroxy-" should read -- -4-hydroxy- --.

Column 18, line 65 (Claim 41), reading "(±)α-a mino-" should read -- (±)α-amino- --.

Signed and Sealed this

Thirteenth Day of October, 1992

Attest:

DOUGLAS B. COMER

*Attesting Officer*   Acting Commissioner of Patents and Trademarks